(12) United States Patent
Duncan et al.

(10) Patent No.: US 6,338,843 B1
(45) Date of Patent: Jan. 15, 2002

(54) BIOLOGICALLY ACTIVE MATERIALS

(75) Inventors: Ruth Duncan, London; James Cassidy, Torphins; Lisa German, Cardiff; Dale Hirst, Wiltshire, all of (GB)

(73) Assignee: ML Laboratories, Liverpool (GB)

( * ) Notice: Subject to any disclaimer, the term of this patent is extended or adjusted under 35 U.S.C. 154(b) by 0 days.

(21) Appl. No.: 09/445,793

(22) PCT Filed: Jun. 12, 1998

(86) PCT No.: PCT/GB98/01567

§ 371 Date: Mar. 23, 2000

§ 102(e) Date: Mar. 23, 2000

(87) PCT Pub. No.: WO98/56424

PCT Pub. Date: Dec. 17, 1998

Related U.S. Application Data

(60) Provisional application No. 60/054,277, filed on Jul. 30, 1997.

(30) Foreign Application Priority Data

Jun. 12, 1997 (GB) .............................................. 9712100

(51) Int. Cl.[7] .......................... A61K 31/74; A61K 9/14; A61K 31/70; A61K 31/715
(52) U.S. Cl. .................... 424/78.18; 424/486; 424/488; 514/23; 514/54; 514/58
(58) Field of Search .............................. 424/78.18, 1.53, 424/1.1, 85.91, 488, 646; 514/58, 54, 60, 492, 59

(56) References Cited

U.S. PATENT DOCUMENTS

| 4,496,689 A | | 1/1985 | Mitra |
| 4,793,986 A | * | 12/1988 | Serino et al. .............. 424/1.53 |
| 5,439,892 A | * | 8/1995 | Davies ......................... 514/58 |

FOREIGN PATENT DOCUMENTS

| EP | 540751 | * 11/1992 |
| EP | 0 540 751 A1 | 5/1993 |
| FR | 2 346 016 | 10/1977 |
| JP | 57056500 | * 4/1982 |
| WO | WO 92/04904 | 4/1992 |
| WO | WO-9404159 | * 3/1994 |
| WO | WO 95/05199 | 2/1995 |
| WO | WO 95/34325 | 12/1995 |

OTHER PUBLICATIONS

Duncan et al., Dextrins as Carriers of Anticancer Agents, Proceed Int'l. Symp. Control Rel. Bioact. Mater., 24; 771–772 (1997).

(List continued on next page.)

Primary Examiner—Thurman K. Page
Assistant Examiner—Blessing Fubara
(74) Attorney, Agent, or Firm—Klarquist Sparkman LL

(57) ABSTRACT

A polymer-drug conjugate, in which the polymer is the polysaccharide dextrin, linked directly or indirectly to the drug, is effective to deliver the drug to a target site and is biodegradable. The conjugate may be prepared by succinoylating dextrin followed by reaction with the drug or a derivative thereof.

32 Claims, 15 Drawing Sheets

OTHER PUBLICATIONS

Nakhapetayan et al., Thermostability of Soluble and Immobilized Subtilisins After Their Modification by Dextrans and Dextrins, *Enzyme Eng.*, 5; 423–426 (1980).

Seymour et al., Tumour Tropism and Anti–Cancer Efficacy of Polymer–Based Doxorubicin Prodrugs in the Treatment of Subcutaneous Murine B16F10 Melanoma, *Br. J. Cancer*, 70; 636–641 (1994).

Gerrit et al., Preparation, Characterization, and Pharmaceutical Application of Linear Dextrins. II. Complexation and Dispersion of Drugs with Amylodextrin by Freeze–Drying and Kneading, *Pharmaceutical Research*, 10; 9 1280–1284 (1993).

List et al., Hagers Handbuch Der Pharmazeutishen Praxis, *Springler Verlag*, Berlin–Heildelber–New York, 3: 61–65 (1972).

Kawasaki et al., Preparation of Protein–Polysaccharide Conjugates As Pharmaceuaticals and Cosmetics, *Database Chemabs Chemical Abstracts Service*, abstract No. 120: 135152 (1993).

* cited by examiner

BIOLOGICALLY ACTIVE MATERIALS

This appln is a 371 of PCT/GB98/01567 filed Jun. 12, 1998, which claims benefit of Prov. No. 60/054,277 filed Jul. 30, 1997.

FIELD OF THE INVENTION

This invention relates to biologically active materials, and, in particular, to materials which comprise a polymer linked to a biologically active agent. The invention is concerned with materials known as polymer-drug conjugates which typically contain a therapeutic agent, in particular, an anti-cancer drug, linked to a polymer backbone. The linkage between the polymer and the drug is by covalent bonding.

BACKGROUND OF THE INVENTION

In designing a polymer-drug conjugate, the aim is to deliver a drug effectively to a therapeutic site such as a tumour. It is known, for instance, that polymer-drugs given intravenously can accumulate selectively in solid tumour tissue by the EPR effect.

The most commonly used anticancer agents are low molecular weight compounds which readily gain access to cells by rapid passage across the cell membrane. After intravenous (IV) administration, a large percentage of the injected dose leaves the circulation within a few minutes, resulting in a ubiquitous body distribution of drug and little selective concentration in tumour tissue. By creating a macromolecular polymer-anticancer drug conjugate, there is provided an opportunity to improve tumour specific targeting, to minimise drug entry into sites of toxicity, to control precisely the rate of drug liberation at the target site (giving opportunities for long-term controlled release) and deliver the active principal intracellularly, providing a means to overcome p-glycoprotein related multidrug resistance.

Numerous polymers have been proposed for synthesis of polymer-drug conjugates including polyaminoacids, polysaccharides such as dextran, and synthetic polymers such as N-(2-hydroxypropyl)methacrylamide (HPMA) copolymer. However, these polymers have limitations. For example, a dextran-doxorubicin conjugate has been tested clinically and been found to be much more toxic than the parent drug and the HPMA copolymers which have been clinically tested have the disadvantage of being non-biodegradable in the main chain.

STATEMENTS OF INVENTION

The present invention provides a polymer-drug conjugate in which the polymer is the polysaccharide dextrin. The polymer-drug conjugate may be one in which the polymer is linked directly to the drug or one in which the polymer is linked indirectly to the drug, for instance, by means of a "biodegradable spacer" to which both the drug and the polymer are linked. The dextrin is preferably a non-cyclic dextrin.

It has been found that dextrin is not only a suitable material for forming a biocompatible polymer-drug conjugate capable of delivering a drug to a target site and of releasing the drug at such a site but is also biodegradable in a manner such that it may be used at a molecular weight which is suitable for the particular drug and its application without any upper limit imposed by the need to ensure excretion of the polymer.

The term "dextrin" means a glucose polymer which is produced by the hydrolysis of starch and which consists of glucose units linked together by means mainly of alpha-1,4 linkages. Typically dextrins are produced by the hydrolysis of starch obtained from various natural products such as wheat, rice, maize and tapioca. In addition to alpha-1,4 linkages, there may be a proportion of alpha-1,6 linkages in a particular dextrin, the amount depending on the starch starting material. Since the rate of biodegradability of alpha-1,6 linkages is typically less than that for alpha-1,4 linkages, for many applications it is preferred that the percentage of alpha-1,6 linkages is less than 10% and more preferably less than 5%.

Any dextrin is a mixture of polyglucose molecules of different chain lengths. As a result, no single number can adequately characterise the molecular weight of such a polymer. Accordingly various averages are used, the most common being the weight average molecular weight (Mw) and the number average molecular weight (Mn). Mw is particularly sensitive to changes in the high molecular weight content of a polymer whilst Mn is largely influenced by changes in the low molecular weight of the polymer.

It is preferred that the Mw of the dextrin is in the range from 1,000 to 200,000, more preferably from 2,000 to 55,000.

The term 'degree of polymerisation' (DP) can also be used in connection with polymer mixtures. For a single polymer molecule, DP means the number of polymer units. For a mixture of molecules of different DP's, weight average DP and number average DP correspond to Mw and Mn. In addition DP can also be used to characterise a polymer by referring to the polymer mixture having a certain percentage of polymers of DP greater than a particular number or less than a particular number.

It is preferred that, in the dextrin-drug conjugate of the present invention, the dextrin contains more than 15% of polymers of DP greater than 12 and, more preferably, more than 50% of polymers of DP greater than 12.

The drug loading on the polymer is preferably from 0.5 to 99.5 mole %.

A targeting group may be attached either directly or indirectly to the polymer of the conjugate. It is preferred that the ratio of drug to targeting group is from 1:99 to 99:1.

Preferably the dextrin used in a dextrin-drug conjugate of the present invention is water soluble or at least forms a suspension in water.

The dextrin of a dextrin-drug conjugate of the invention may be in the form of either unsubstituted dextrin (as obtained by the hydrolysis of the starch) or may be substituted by one or more different groups. The substituents may be negatively charged groups, for instance, sulphate groups, neutral groups or positively charged groups, for instance, quaternary ammonium groups. In the case where the substituent group is sulphate, it is preferred that the sulphated polysaccharide contains at least one sulphate group per saccharide (glucose) unit. A particular dextrin sulphate is dextrin-2-sulphate.

Examples of drugs which may form suitable conjugates with dextrin are:- alkylating agents such as cyclophosphamide, melphalan and carmusline; antimetabolites such as methotrexate, 5-fluorouracil, cytarabine and mercaptopurine; natural products such as anthracyclines (eg daunorubicin, doxorubicin and epirubicin), vinca alkaloids (eg vinblastine and vincristine) as well as dactinomycin, mitomycin C, taxol, L-asparaginase and G-CSF; and platinum analogues such as cisplatin and carboplatin.

The present invention also provides a pharmaceutical composition comprising a dextrin-drug conjugate and a pharmaceutically acceptable excipient or diluent therefor.

In addition, the present invention provides the use of a polymer-drug conjugate of the invention in the treatment of a medical condition in connection with which the drug is effective, Furthermore, the invention provides the use of a polymer-drug conjugate of the invention in the manufacture of a medicament for use in the treatment of a medical condition in connection with which the drug is effective.

The present invention also provides a method of treating an animal subject, including a human being, including treating the animal subject with a pharmaceutically effective dose of a dextrin-drug conjugate. The conjugate may be administered by any appropriate method, for instance, intravenously, intraperitoneally, orally, parentally or by topical application.

Various methods have been proposed for the preparation of polymer-drug conjugates. Within the scope of the present invention is a method comprising succinoylating dextrin and reacting the succinoylated dextrin with a drug or reactive derivative thereof.

Preferably, the dextrin is dissolved in anhydrous dimethyl formamide and is contacted with dimethyl amino pyridine and succinic anhydride. The resultant mixture is then purged with an inert gas and chemical reaction is allowed to take place over a prolonged period, preferably at least 12 hours.

The resultant succinoylated dextrin is reacted with a drug or drug derivative eg. doxorubicin hydrochloride to form the polymer-drug conjugate.

EXAMPLES OF THE INVENTION

The present invention will now be further described with reference to the following examples. In these examples three dextrin materials are used, their molecular weight characteristics being as follows (Table 1):

TABLE 1

Examples confirming the Biocompatibility of Dextrins

| Code | Mw | Mn | Mw/Mn |
| --- | --- | --- | --- |
| MLD5/29 | 5K | 6K | 2.74 |
| DX04/0G | 15K | 6K | 2.74 |
| MLD15/73 | 51K | 28K | 1.84 |

Example 1

Effect of Dextrins on the Stability of Rat Red Blood Cells Incubated in Vitro.

Method

Figure 1:
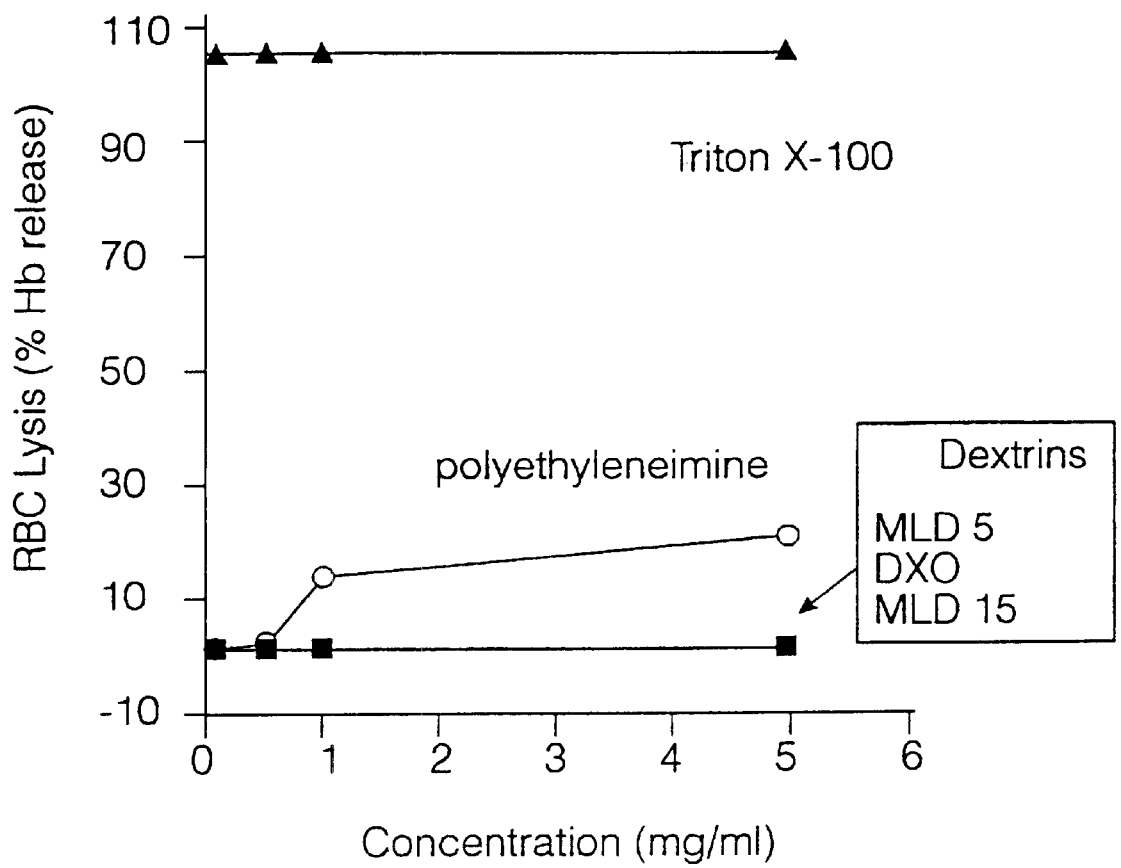
FIG. 1 is a graphical illustration of the effect of dextrins on red blood cell lysis.

Dextrins of different molecular weight were incubated with isolated rat red blood cells (RBC) and haemoglobin release detected spectrophotometrically. Various dilutions of the test polymers (dextrins) and of the reference polymer polyethyleneimine were made up in PBS and mixed with an equal volume of fresh 2% w/v suspension of rat RBCs. This preparation was centrifuged at 1500×g for 10 min at room temperature. Then, 100 μl of the supernatant was removed and the levels of haemoglobin quantitated spectrophotometrically at 5.50 nm. The results illustrated in FIG. 1 were expressed as % lysis relative to that of a Triton X-100 control (Sigma) which gave 100% RBC lysis.

Results

None of the dextrin polymers induced red cell lysis. Polyethyleneimine and the detergent Triton X-100 (control 100% lysis) both caused haemoglobin release.

Example 2

Cytotoxicity of Unmodified Dextrins Against L1210 Cells.

Method

L1210 cells were seeded at a density of $1\times10^4$ cells per well into 96 well 'v' bottomed microtiter plates (Costar) in RPMI 1640 tissue culture media (Gibeo) supplemented with 10% Foetal Calf Serum (FCS) (Gibeo). All incubations were carried out at 37° C. in an atmosphere of 5% $CO_2$.

Figure 2:
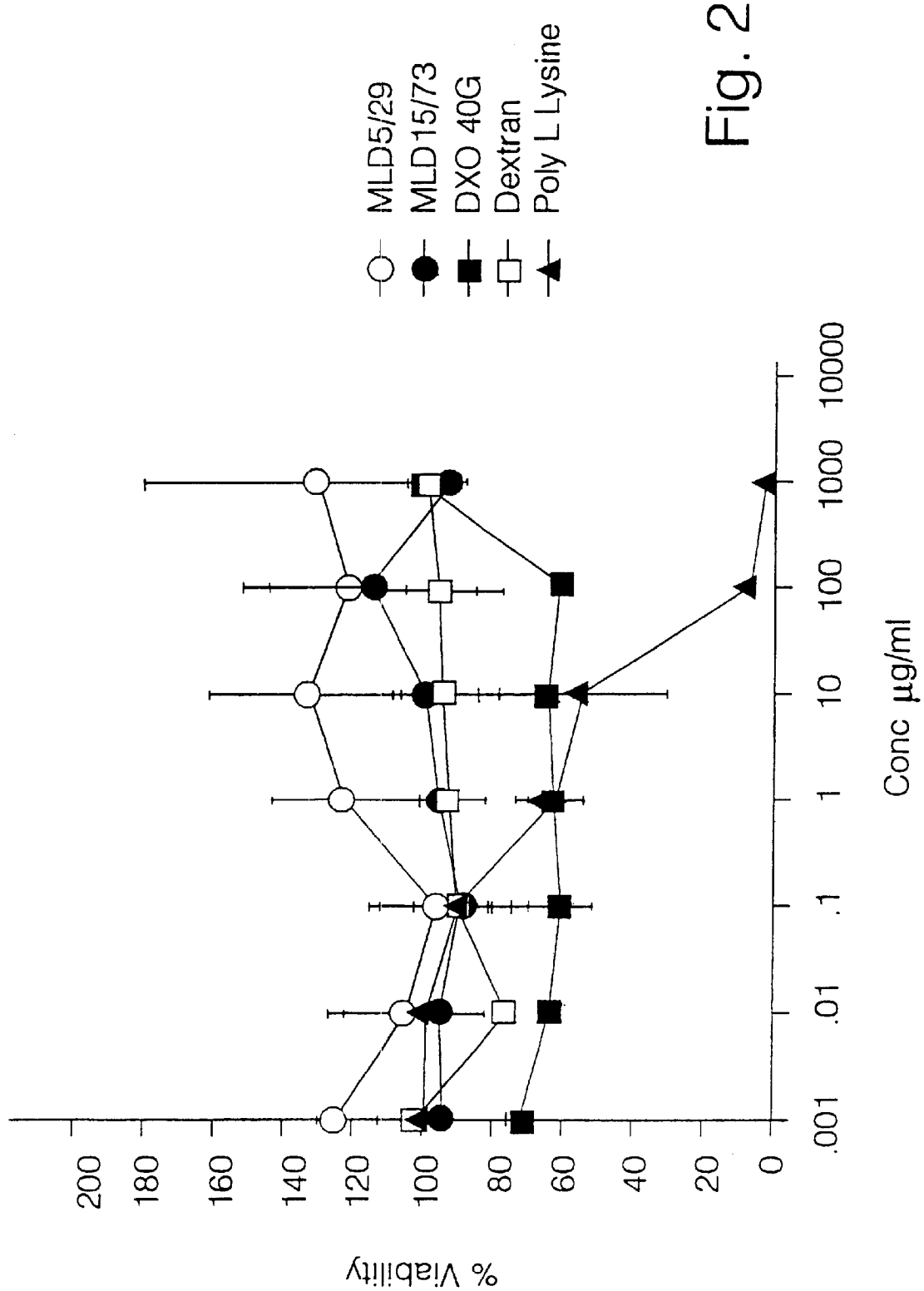
FIG. 2 is a graphical illustration of the effect of compounds MLD 15/73, MLD 5/29 and DXO 40G against Poly L lysine and Dextran.

The cells were then left for 24 h. Prior to being incubated with the polymers, the cells were centrifuged at 1000×g for 10 minutes at room temperature. This served to pellet the cells and allow the removal of the media. The polymers were then dissolved in RPMI 1640 containing 10% FCS and filter sterilised through 0.2μ filters (Aerodisk). Following this, the pellet was resuspended in media containing the appropriate concentration of the dextrins of different molecular weight. Positive and negative reference controls were incorporated, dextran Mw 72 000 (Sigma) as a negative control and poly(L-Lysine) Mw 56 500 (Sigma) as a positive control. These polymers were added to cells at the same concentrations as the test polymers. The tetrazolium dye MTT was used to assess cell viability. The cells were then incubated for 67 h prior to the addition of the MTT. After a further incubation period of 5 h, the cells in suspension were subjected to centrifugation, the media removed and 100 μl of optical grade DMSO (Sigma) added. The plates were read at 550 mn using a Titerteck plate reader. The results are illustrated in FIG. 2. The % viabilities are optical densities (OD's) expressed as a % of the OD seen in cell cultures containing no polymer.

Results

None of the dextrins was cytotoxic. The toxic effect of the reference control poly-L-Lysine can be seen.

Examples Relating to Dextrin Modification for Coupling of Pendent Groups

To bind pendent drugs or side chains to dextrins there are a number of possible activation methods that may be used. These include:

a) Periodate Oxidation

This is a ring opening method resulting in polyaldehyde derivatives of a polysaccharide (Bruneel and Schacht 1992). Unfortunately this reaction is prone to a number of side reactions that makes the production of single, pure, easily characterised compound quite difficult. In particular there is evidence for the formation of intra-residual hemiacetal formation. However, when formed aldehyde groups represent sites where amines can be attached to the polymer in the form of Schiff base structures or alkyl amines.

b) The 4-nitrophenyl Chloroformate Method

This is easily carried out at 0° C. and there is much information available on the analysis of the various groups that do, or do not, react. Clean up/purification procedures would appear to be straightforward and percentage reactivity of active groups in the range of interest would appear to be controllable to an effective extent. There is some concern, however, over the formation of undesirable five membered cyclic carbonates (Bruneel and Schacht 1992).

c) Succinoylation

Activation by succinoylations is also an easily performed operation. The conditions employed are however somewhat acerbic by comparison with the chloroformate method. The initial reaction requires refluxing at 40° C. for 24 hr in dry DMSO, but results in the formation of carbonate functionalities. This reaction also includes an extra step on the way to the production of the amine derivative by virtue of going through an intermediate step involving N,N'-carbonyldiimidazol. Here too, purification would appear to be relatively uncomplicated.

d) Cyanogen Bromide Activation

Activation by cyanogen bromide is easily carried out in aqueous conditions at room temperatures. (Immobilised Affinity Ligand Techniques, Herman GT, Mallia AK and Smith PK. Pub: Academic Press, New York, 1992). Excess reagent must however be neutralised and eliminated as it may liberate hydrogen cyanide in an acidic environment. In addition to this side reactions may occur resulting in several reactive intermediates. It does however have advantages in that a primary amine can be introduced directly on the reactive intermediate. Finally there is evidence for the linkage being unstable resulting in slow release of the pendant group which may or may not be advantageous or desirable.

Examples

Modification of Dextrins by Succinoylation and Reaction with Compounds Containing Amino Groups ( in relation to (c) above).

All three dextrin samples were modified by means of succinoylation. Initially, attempts to modify the samples to the extent of 50, 20, 10, 5, 2.5 and 1 mol% were carried out. The sample with the highest molecular weight was taken forward for further reaction with tyrosinamide and doxorubicin.

Example 3.1

Synthesis of Succinoylated Dextrins

In triplicate batches of dextrin (1 g, MD 15/73, $1.94 \times 10^{-5}$ mol) was dissolved in anhydrous dimethyl formamide (DMF, 10 m). Dimethyl amino pyridine (DMAP, 28.3 mg) was then added followed by succinic anhydride (62 mg, $6.2 \times 10^{-1}$ mol, 10 mol %). The mixture was then purged with nitrogen, sealed and left to stir for 24 h at temperatures of 20, 30, 40 and 50° C. Following this the reaction mixture was poured onto rapidly stirring diethyl ether (100 ml) and magnetically stirred overnight. The ether was then removed by filtration under vacuum and the resulting solid dissolved into a minimum of distilled water poured into a dialysis membrane (Visking tubing, MW cut-off 12000–1400) and purified by dialysis against 2×2L of distilled water. The resulting solution was freeze dried and recovery calculated. Degree of succinoylation was the determined by titration against a relevant standard of NaOH. After application of the students T-Test there was no difference in the degree of succinoylation for any reaction condition. Results are shown in Table 2.

TABLE 2

Results of the effect of temperature on the succinoylation of dextrin

| Temperature | % Recovery (g) (± SD) | Mol % Succinoylation (± SD) |
| --- | --- | --- |
| 20 * | ND | ND |
| 30 | 53.3 (6.7) | 6.64 (0.74) |
| 40 | 73.4 (10.7) | 5.49 (0.32) |
| 50 | 42.6 (12.3) | 2.26 (0.12) |

* Did not dissolve

As an alternative procedure the product may be purified by gel filtration, ultrafiltration or centrifugation against a pore controlled membrane.

The same reaction conditions (adjusting the ratios of the components or solvents) were used to achieve degrees of succinoylation of the dextrin samples of different molecular weights (MW 4950, 15000 and 51,100). See Table 1.

Example 3.2

Conjugation of Doxorubicin to Succinoylated Dextrins

Succinoylated dextrin (51 mg, $1 \times 10^{-6}$ mol, MD 15/73, 5.3 mol % succinoylation) was dissolved in 2 ml of distilled water, to this was added EDC (3.51 mg $1.8 \times 10^{-5}$ mol). This was allowed to react at room temperature while gently stirring for 30 min. After this time Doxorubicin hydrochloride (Pharmacia) was added (9.67 ml of a 1 mg ml$^{-1}$ solution. $1.67 \times 10^{-5}$ mol). The reaction vessel was wrapped in foil and allowed to stir overnight at room temperature. The product was isolated by solvent extraction with chloroform and passage over a LH 20 superdex column (Pharmacia) followed by freeze drying to constant weight. Finally free and conjugated Doxorubicin was measured by extractive HPLC. Results of various conjugations are summarised in Table 3.

TABLE 3

Incorporation of Doxorubicin on various Dex-Dox Conjugates

| Succinoylation Mol % | Coupling Conditions | Time | Percent W/W incorporation |
|---|---|---|---|
| 0.5 | EDC/Water | Overnight | 0.127 |
| 6.53 | EDC/Water | Overnight | 4.2 |
| 6.53 | CDI/DMF | Overnight | 3.9 |
| 5.3 | CDI/DMF | 4 hours | 2.1 |
| 14.9 | EDC/water/Sulpho-NHS | 4 hours | 6.39 |
| 14.9 | EDC/WATER | 4 hours | 2.82 |

Alternatively Doxorubicin may be conjugated using, Sulpho-NHS and EDC in aqueous conditions to improve coupling yields or with other peptitde coupling agents and solvent of choice.

Figure 3A:
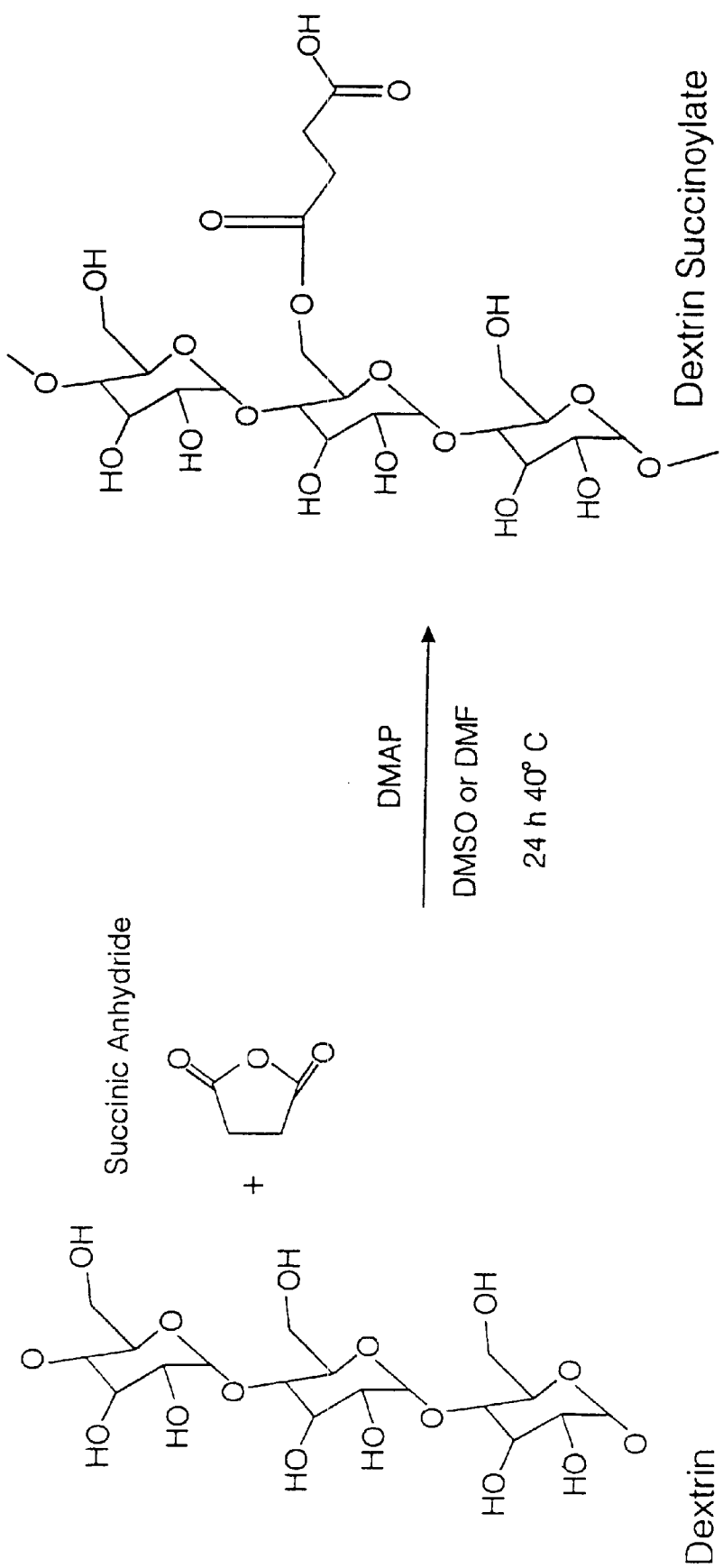
FIGS. 3A and 3B illustrate the synthetic route for the preparation of dextrin-doxorubicin.
Figure 3B:
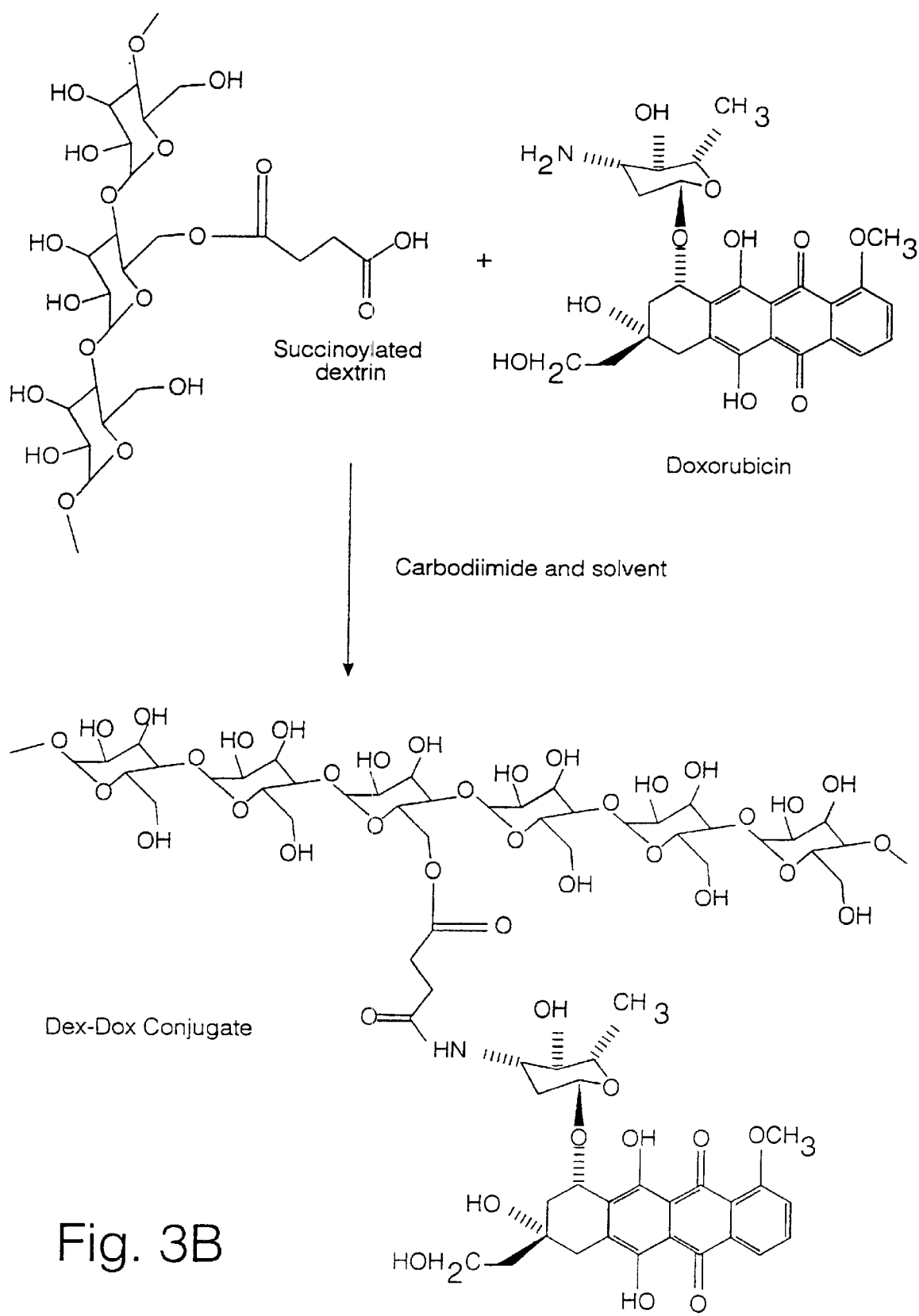

The synthetic route for the preparation of dextrin-doxorubicin is illustrated in FIGS. 3a and 3b.

Example 3.3

Conjugation of Tyrosinamide to Succinoylated Dextrin

Succinoylated dextrin (57.7 mg, MD 15/73, 1 mol%) was dissolved in 3 ml of DMF, to this was added CDI (10.4 mg, $6.4 \times 10^{-5}$ mol) dissolved in DMF (1 ml). This was allowed to react at 25° C. while stirring for 1 h. After this time tyrosinamide (97 mg, $8.96 \times 10^{-4}$ mol was dissolved in DMF (1 ml) and added to the reaction. This was allowed to react stirring at room temperature at 25° C. for 48 h. The product was isolated by removal of the DMF by rotary evaporation. To the product was added water (3 ml) followed by freeze drying until constant weight was maintained. The product was purified by dialysis against distilled water (24 h).

Example 3.4

Conjugation of Biotin Hydrozide to Succinoylated Dextrin

Succinoylated dextrin (57.7 mg, MD 15/73, 1 mol %) was dissolved in 3 ml of DMF, to this was added CDI (10.4 mg, $6.4 \times 10^{-5}$ mol) dissolved in DMF (1 ml). This was allowed to react at 25° C. while stirring for 1 hour. After this time biotin hydrozide (97 mg, $8.96 \times 10^{-1}$ mol was dissolved in DMF (1 ml) and added to the reaction. This was allowed to react stirring at room temperature at 25° C. for 48 hour. The product was isolated by removal of the DMF using by rotary evaporation. To the product was added water (3 ml) followed by freeze drying until constant weight was maintained. The product was purified by dialysis against distilled water (24 h).

Example 4

Evaluation of the Cytotoxicity of Doxorubicin and Dextrin-doxorubicin Conjugates Method L1210 cells were seeded at a density of $1 \times 10^4$ cells per well into 96 well 'v' bottomed microtiter plates (Costar) in RPMI 1640 tissue culture media (Gibeo) supplemented with 10% Foetal Calf Scrum (FCS) (Gibeo). All incubations were carried out at 37° C. in an atmosphere of 5% $CO_2$.

The cells were then left for 24 h. Prior to being incubated with the polymers the cells were centrifuged at 1000×g for 10 minutes at room temperature. This served to pellet the cells and allow the removal of the media.

Doxorubicin and dextrin doxorubicin were then dissolved in RPMI 1640 containing 10% FCS and filter sterilised through $0.2\mu$ filters (Aerodisk). Following this, the pellet was resuspended in media containing the appropriate concentration of drug or drug conjugate.

Figure 4:
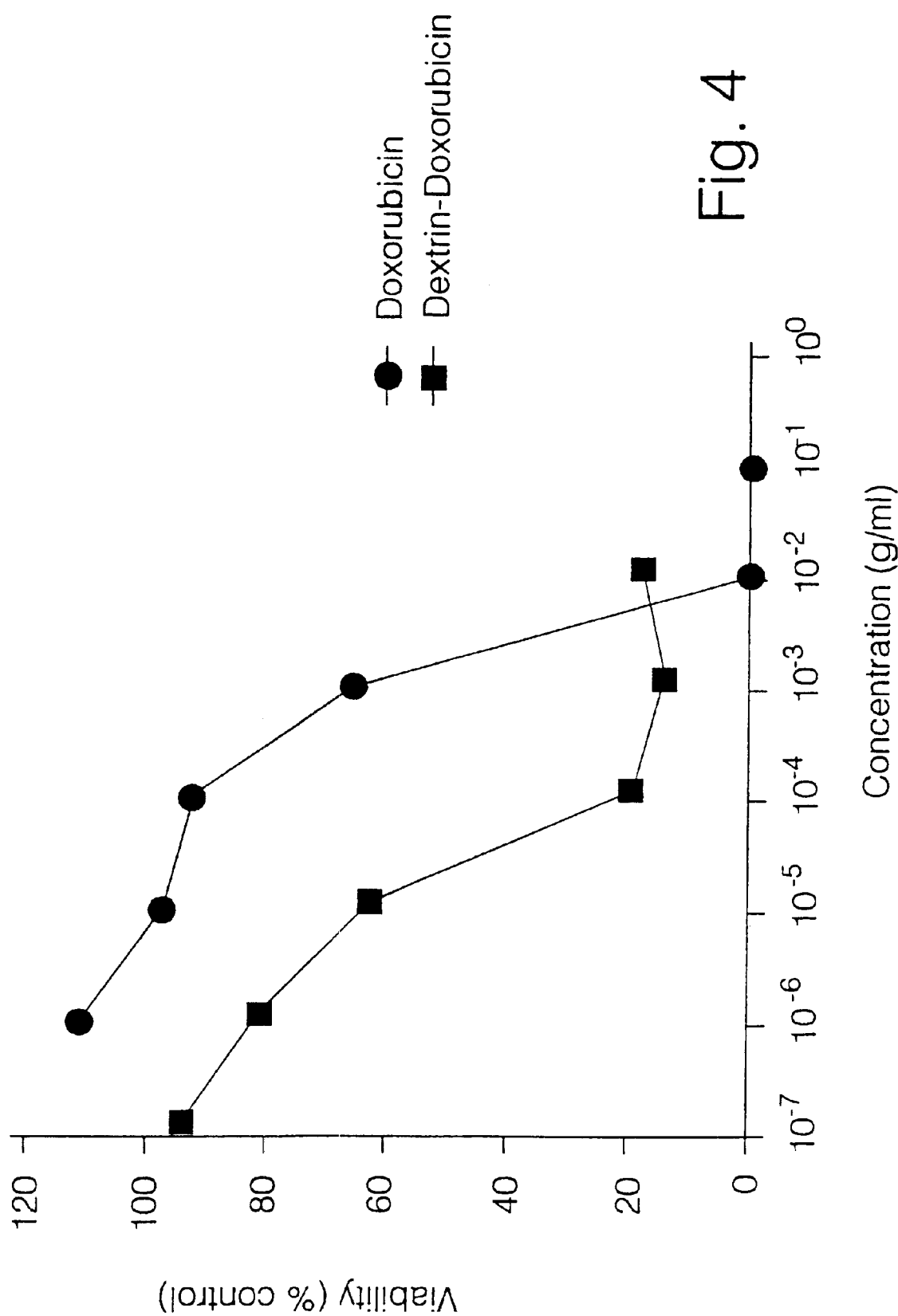
FIG. 4 is a graphical illustration of the cytotoxicity of doxorubicin and a dextrin-dox conjugate against L1210 cells (72 h).

The tetrazolium dye MTT was used to assess cell viability. The cells were incubated for 67 h prior to the addition of the MTT. After a further incubation period of 5 h, the cells in suspension were subjected to centrifugation, the media removed and 100 $\mu$l of optical grade DMSO (Sigma) was added. The plates were read at 550 mn using a Titerteck plate reader. Results (OD) were expressed as a % of the OD seen in cell cultures containing no polymer. They are illustrated in FIG. 4.

Results

It can be seen that both doxorubicin and the dextrin doxorubicin conjugate (prepared in example 3.2) were toxic to L1210 cells in vitro. This confirms that active doxorubicin can be released from the conjugate over the 72 h incubation period. It is not surprising that the conjugate is less active than the parent drug in vitro. This is a well known phenomenon attributed to the very slow capture of a polymeric drug by cells by the mechanism of endocytosis. Free doxorubicin penetrates the cell immediately by passing across the cell membrane.

Example 5

Experiments to Demonstrate the Targeting on Dextrin-doxorubicin to sc. B16F10 (mouse melanoma)

Method

C57 black mice were injected subcutaneously (sc) with $10^5$ B16F10 melanoma cells in normal saline (100 $\mu$l). The mice were checked daily for the appearance of tumours and when palpable (10–13 days) the mice were then injected iv with dextrin-doxorubicin (6.0 wt % dox) at a dose of 5 mg/kg dox-equivalent. The mice were culled after 1 min, 1 and 24 h and the tumours were removed, weighed and homogenised in double distilled water (2 ml). The total doxorubicin content was measured by HPLC after acid hydrolysis and extraction into 4:1 chloroform:isopropyl alcohol. Doxorubicin content was then expressed as $\mu$g dox/per g of tumour.

Results

Figure 5:
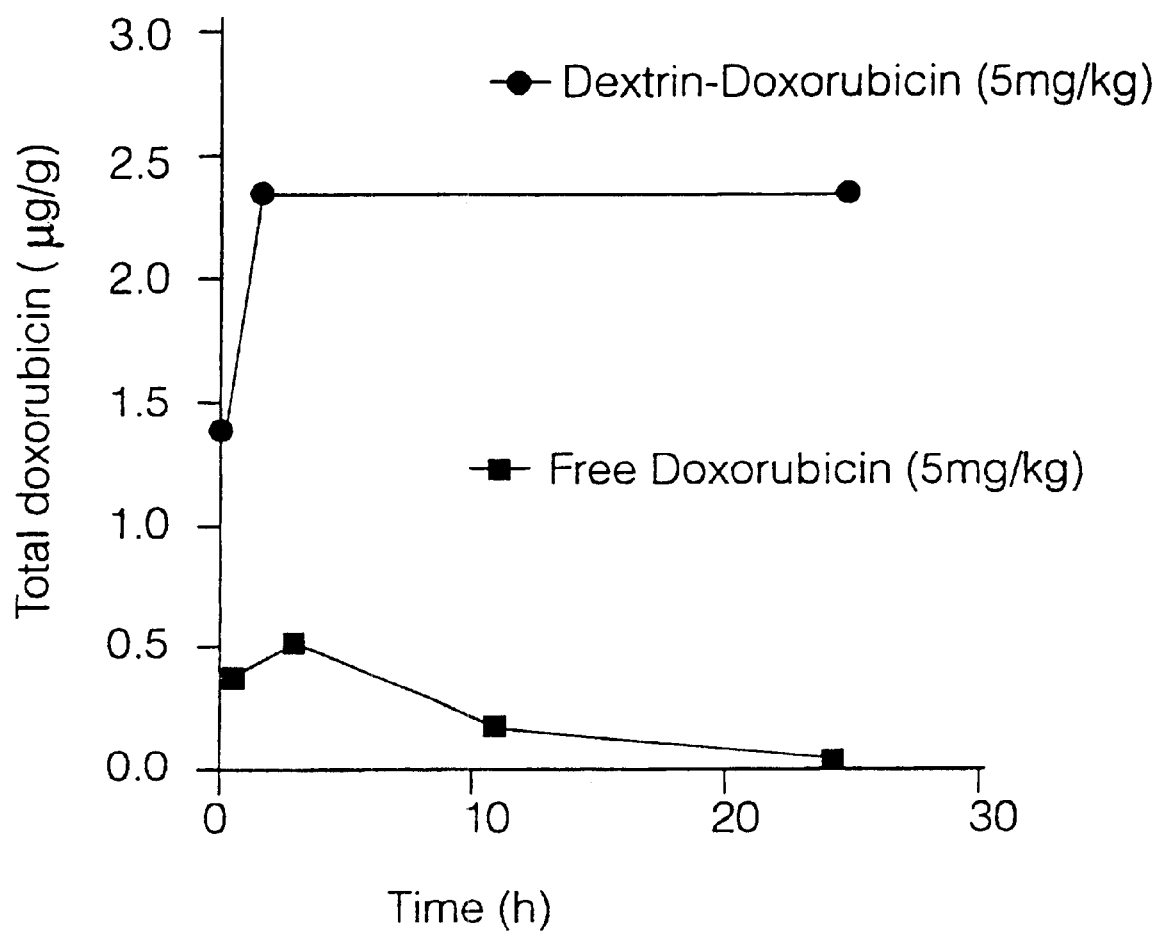
FIG. 5 is a graphical illustration of tumour levels of doxorubicin after administration of dextrin-doxorubicin and free doxorubicin.

After administration of dextrin-doxorubicin no signs of toxicity were observed. It can be seen that administration of drug as a dextrin conjugate resulted in significantly higher tumour levels than seen following administration of free drug (FIG. 5).

Example 6

Radiolabelling of Dextrin-tyrosinamide

Method

To allow monitoring of body distribution and rate of degradation the highest molecular weight dextrin-TyrNH2 was labelled using the Chloramine T method.

Dextrin-tyrosinamide (5 mg) was dissolved in phosphate buffer (0.5 ml. 0.05 M. pH7.0. Na[$^{125}$I]iodide (5 $\mu$l, 5 mCi) was added to the reaction vessel and was left stirring for 2 min. Chloramine T (75 $\mu$l, 2 mg/ml) was added and left stirring for 15 min. Sodium metabisulphate (500 $\mu$l, 2 mg/ml) and a crystal of potassium iodide was added to the reaction vessel and left for 2 min.

Specific activity and purity was determined by paper electrophoresis. Whatman chromatography paper (5×30 cm strips) were divided into 5 mm strips by pencil (40 strips).

Figure 6:
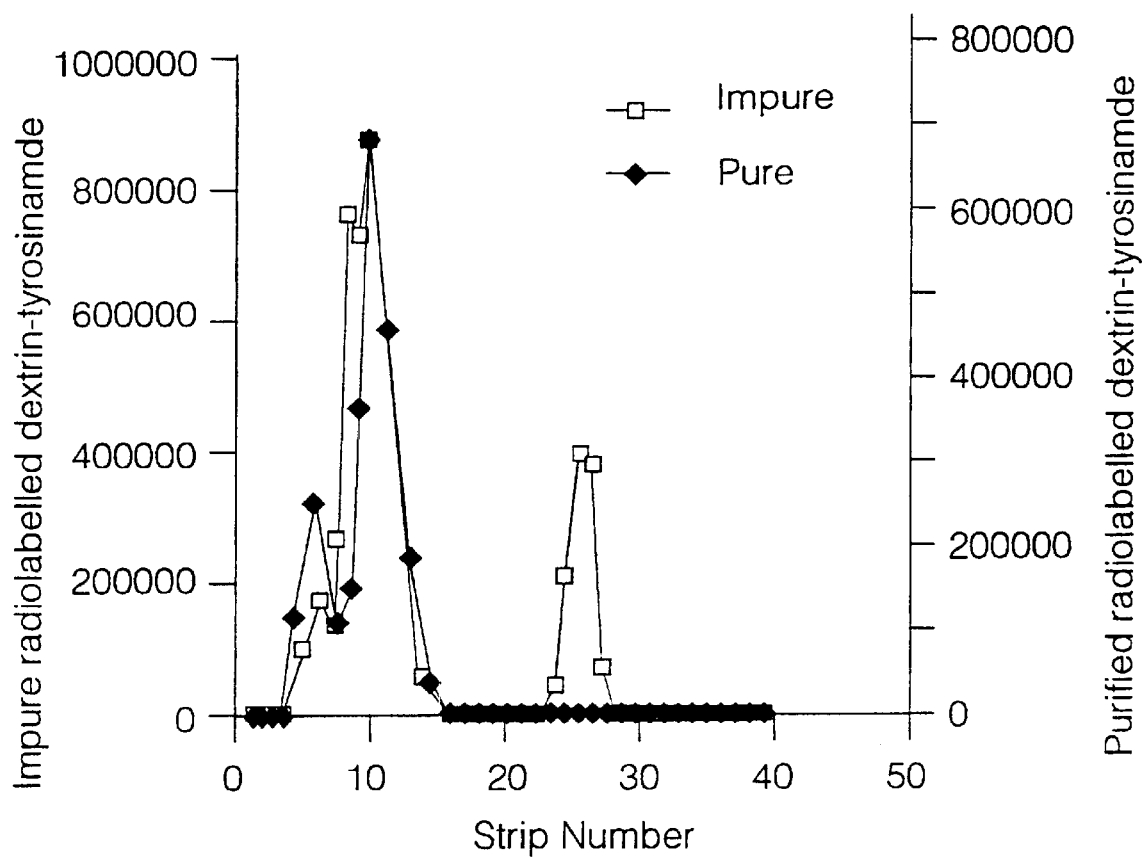
FIG. 6 illustrates an electrophoresis curve for the crude and purified radiolabelled dextrin-tyrosinamide.

Marking the fifth strip as the point of application for the sample. The paper was soaked in barbitone buffer (Sigma B6632) and then blotted dry. Into a paper electrophoresis tank (Shandon) was placed the same buffer and the paper was placed on the supporting bars. Na[$^{125}$I]iodide (4 μl) was placed on the application point nearest the anode as a reference and the crude and pure radiolabelled polymer (4 μl) was placed on the application point nearest the anode as a reference and the crude and pure radiolabelled polymer (4 μl) was loaded onto separate strips. The tank was connected to a power supply and the samples run for 30 min at 400V (constant voltage). The chromatography papers were removed and each 5 mm strip was cut, and placed into counting tubes with 1 ml of water in each and the presence of radioactivity was measured using a gamma counter (Packard). The results were plotted as counts per minute against distance migrated. Results are illustrated in FIG. 6.

Results

The dextrin product was radiolabelled and had a specific activity of approximately 20 μCi/mg.

Example 7

Body Distribution of $^{125}$I-Labelled Dextrin

Figure 7A:
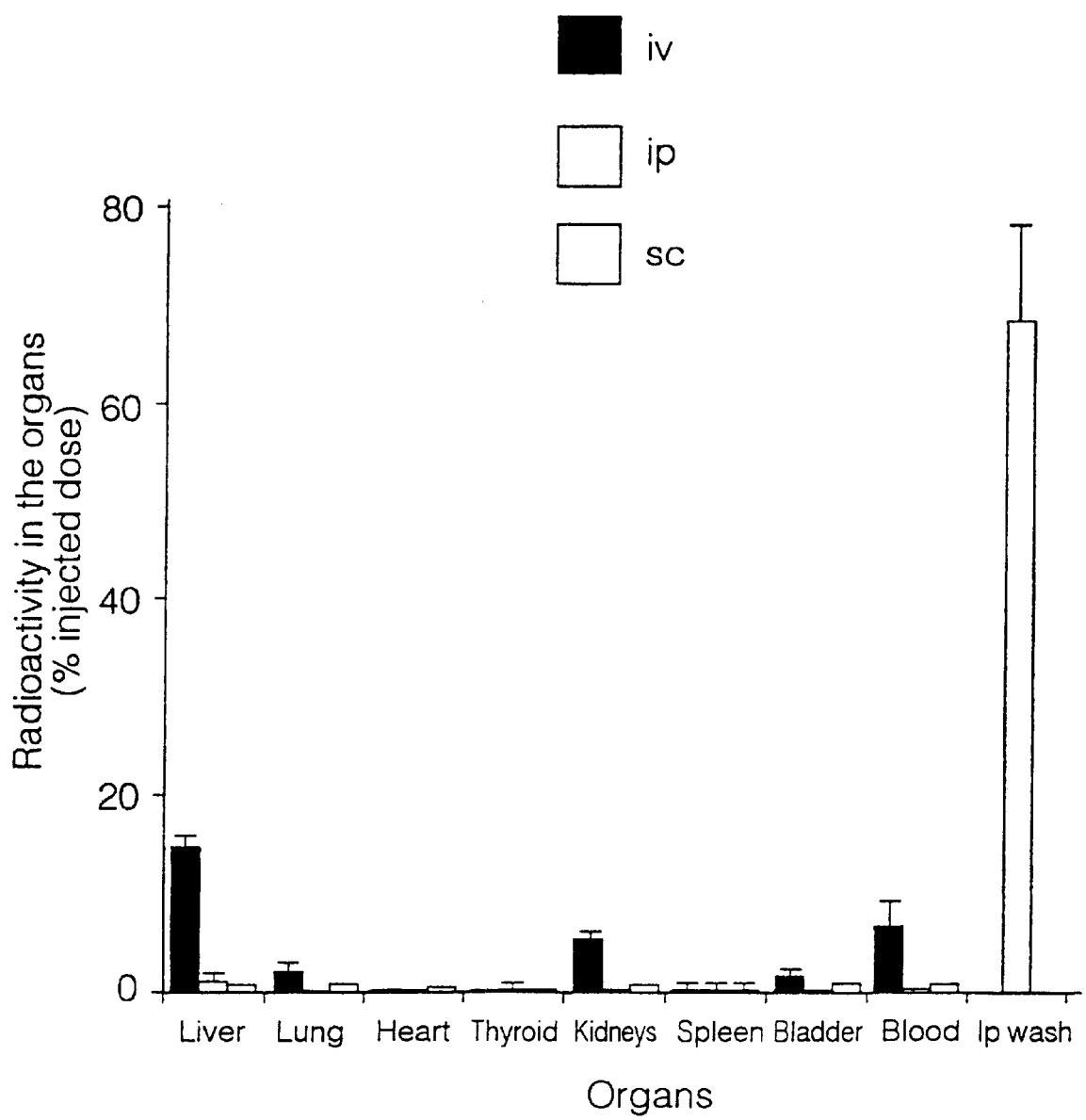
FIGS. 7A, 7B and 7C illustrate body distribution of 125I-labelled dextrin (MW 51000) at 5 minutes, 30 minutes and 1 hour respectively.
Figure 7B:
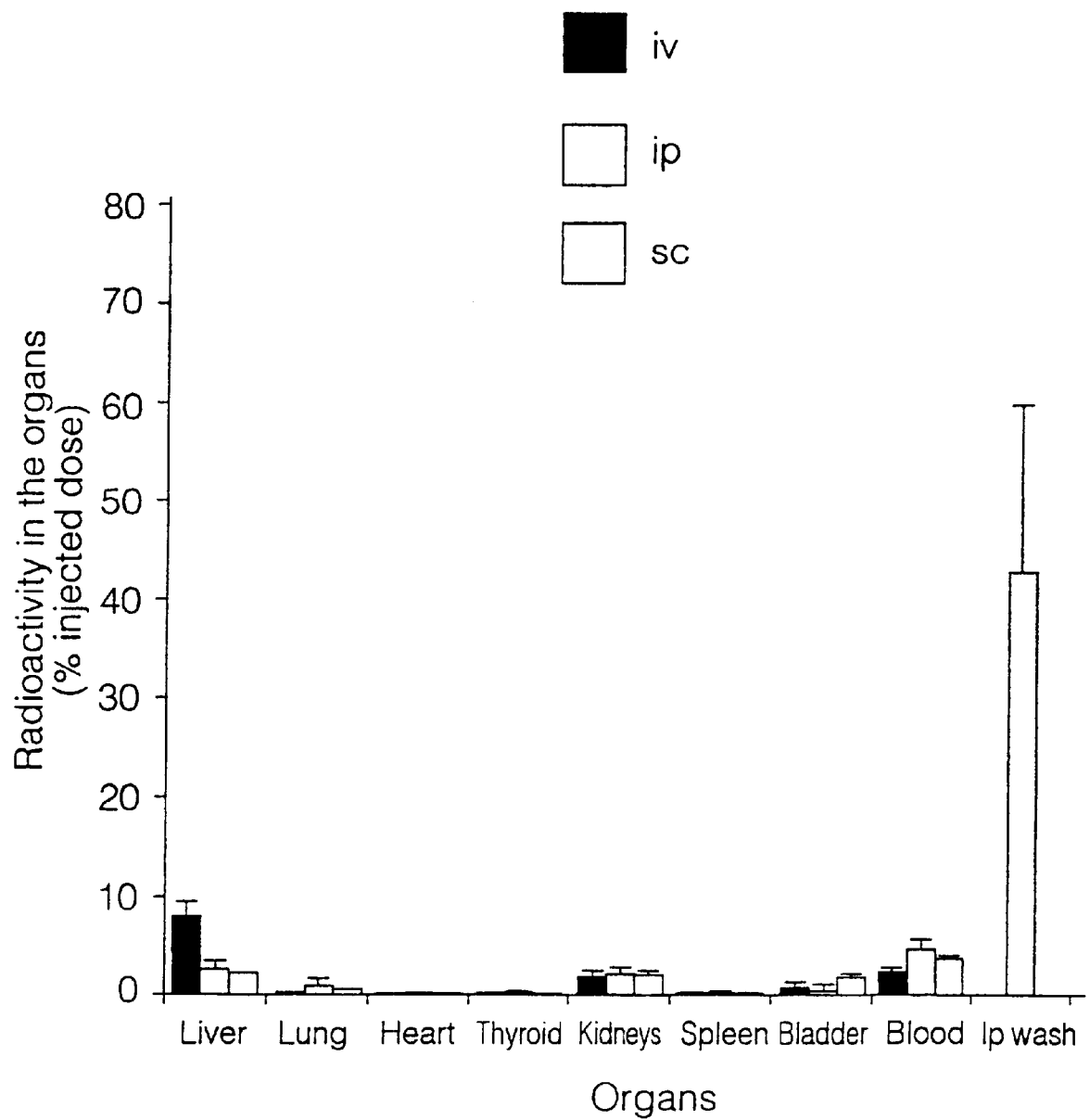
Figure 7C:
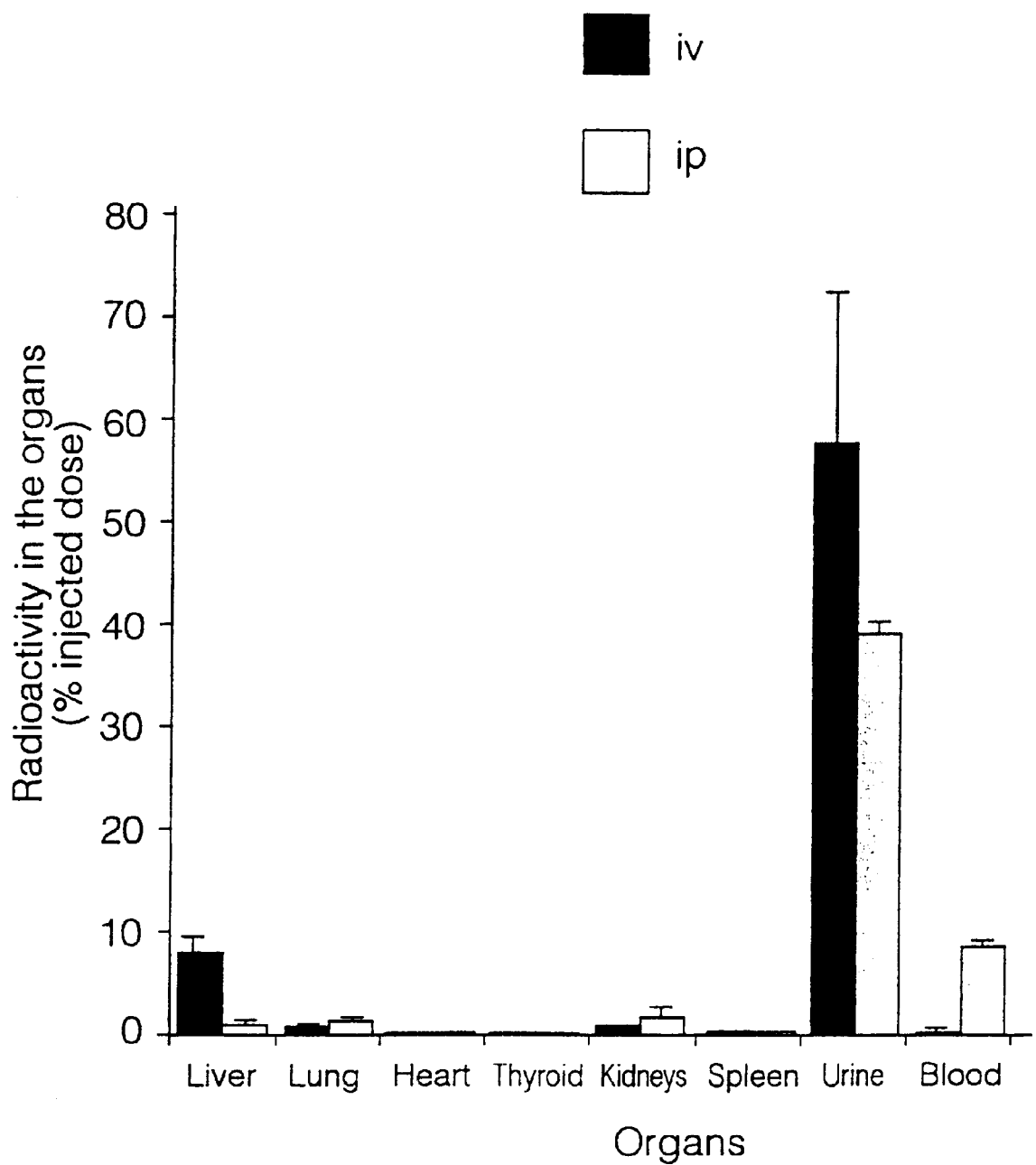

Adult male Wistar rats were anaesthetised with a mixture of oxygen and isoflurothane and radiolabelled dextrin-tyrosinamide (100 μl, specific activity 11.8 μCi/mg) were injected iv, ip or subcutaneous). The rats were culled after the desired time using carbon dioxide. The rat was weighed and all major organs (lungs, heart, liver, kidneys, spleen, thyroid, urine, bladder or blood) were removed. After ip administration a peritoneal wash was also taken. The organs were homogenised in water and samples (1 ml in triplicates) were counted in the gamma counter. The results expressed as % dose injected for each organ are illustrated in FIGS. 7a, 7b and 7c.

Figure 8:
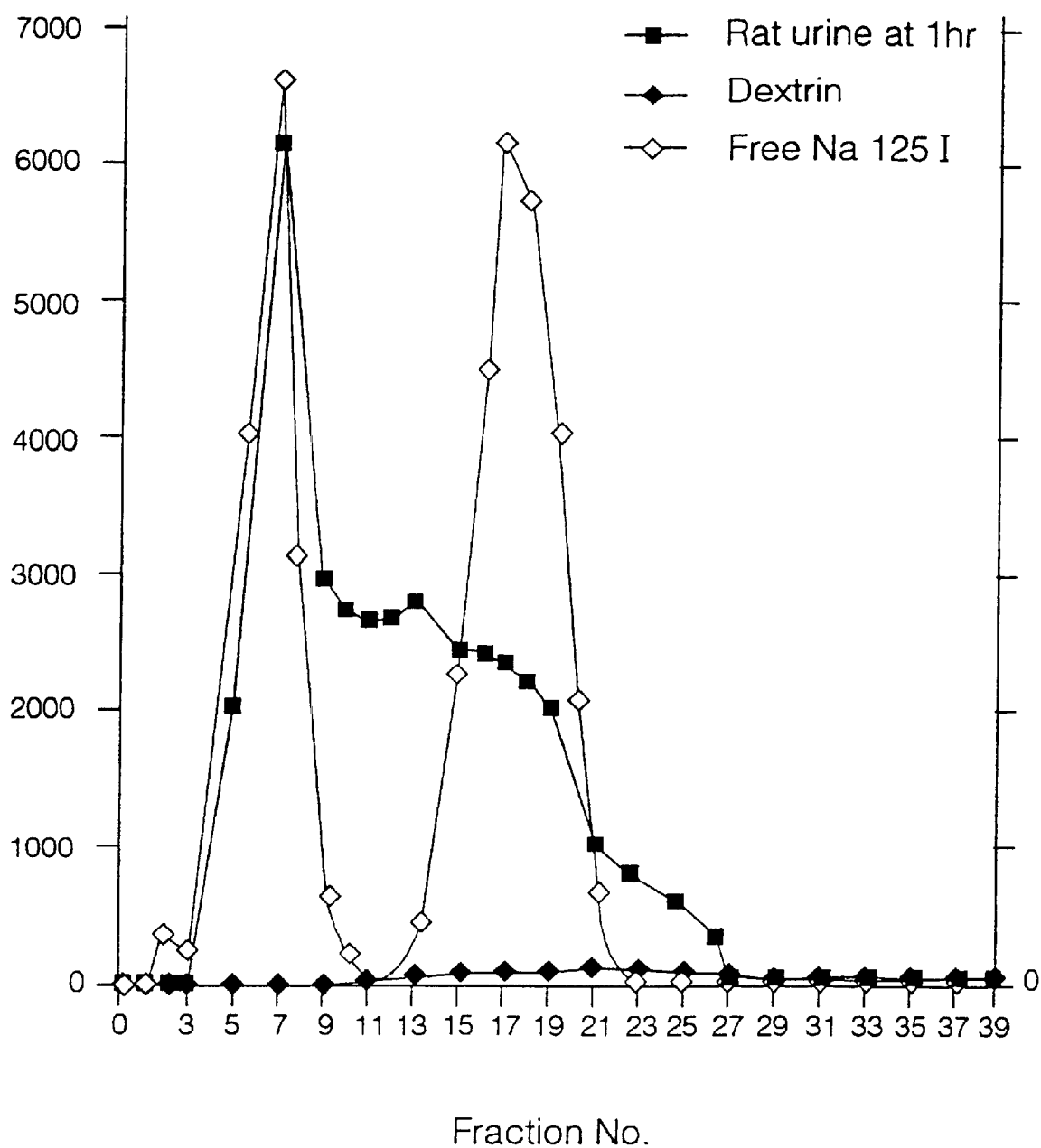
FIG. 8 illustrates the elution of radioactivity from a PD10 Column (Sephadex G-25).

Samples of the urine were subjected to gel permeation chromatography (GPC) using a PD10 column to evaluate the degradation of the polymer in the body. Results are shown in FIG. 8.

Results

After 1 h most of the radioactivity recovered following both ip and iv injection was detected in the urine and faeces. GPC analysis of urine samples indicated liberation of low molecular weight degradation products.

Example 8

Evaluation of the Rates of Hydrolytic and Enzymatic Degradation of Dextrin Samples of Different Molecular Weight Experiments were carried out to determine the stability of the three dextrin samples in physiological buffers (pH 7.4 and 5.5) and also in the presence of enzymes (plasma and lysosomal enzymes (tritosomes).

The molecular weight of the samples and changes with time were monitored by gel permeation chromatography. Two types of experiment were undertaken.

Example 8.1

Degradation of Native and Modified Non-radiolabelled Dextrins by Enzymes followed by HPLC/GPC with RI Detection Method GPC size exclusion was carried out using a TSK G5000 PW and G2000 PW columns in series (7.5×300 mm). The sample injection loop was 20 μl, the mobile phases used were saline phosphate buffer (PBS) at pH 7.4 and later high salt (NaCl 0.25M) citrate buffer at pH 5.5 made with double distilled water in both cases. The eluant flow rate in all cases was 1 ml min$^1$.

Column calibration was carried out with pullulan and glucose molecular weight standards. The method of detection was by means of differential refractometry using a Knauer refractive index detector.

Samples (at concentration of approximately 5 mg ml$^{-1}$) were incubated in the appropriate buffer (with or without enzymes) for several days at 37° C. At various time periods a small sample was taken and subjected to GPC.

Results

Figure 9:
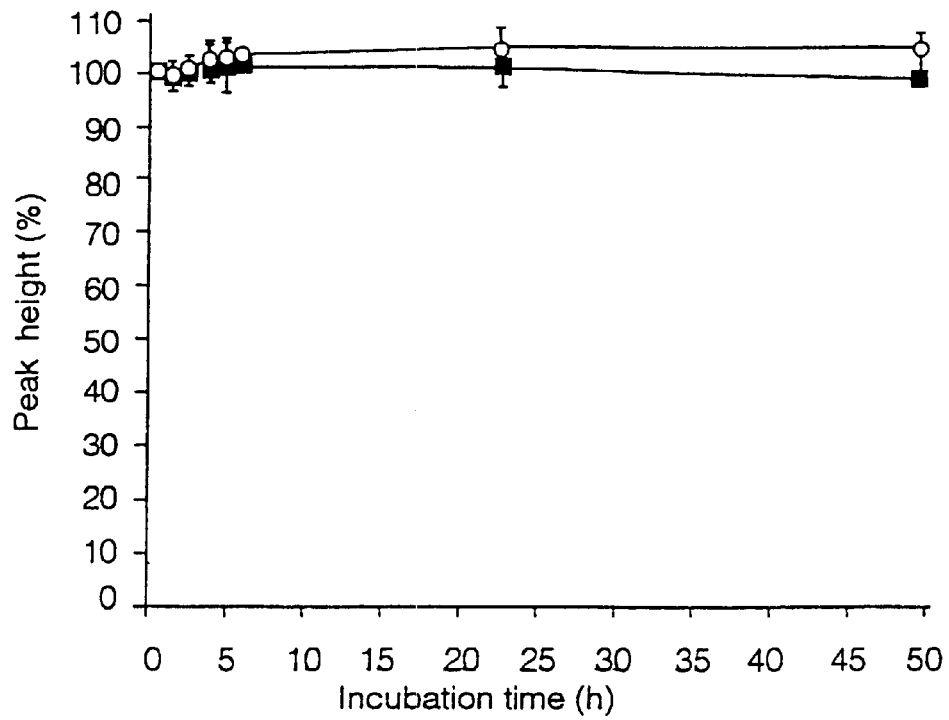
FIG. 9 illustrates the stability of dextrins of different molecular weight in Saline Phosphate Buffer at pH 7.4 without enzymes.
Figure 10:
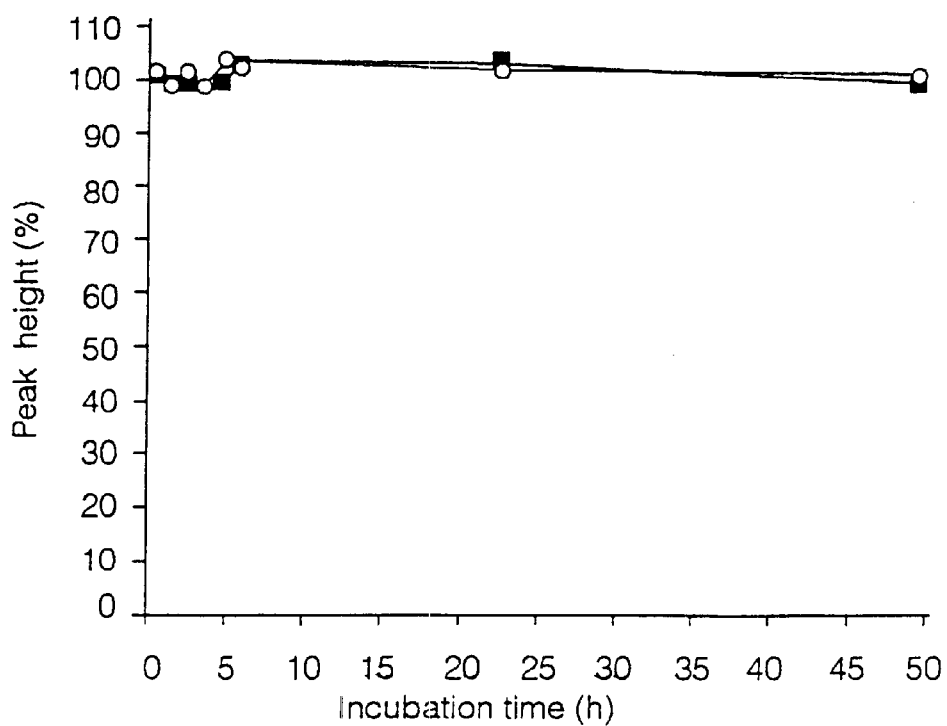
FIG. 10 illustrates the stability of dextrins of different molecular weight in Salt Citrate Buffer at pH 5.5 without enzymes.
Figure 11:
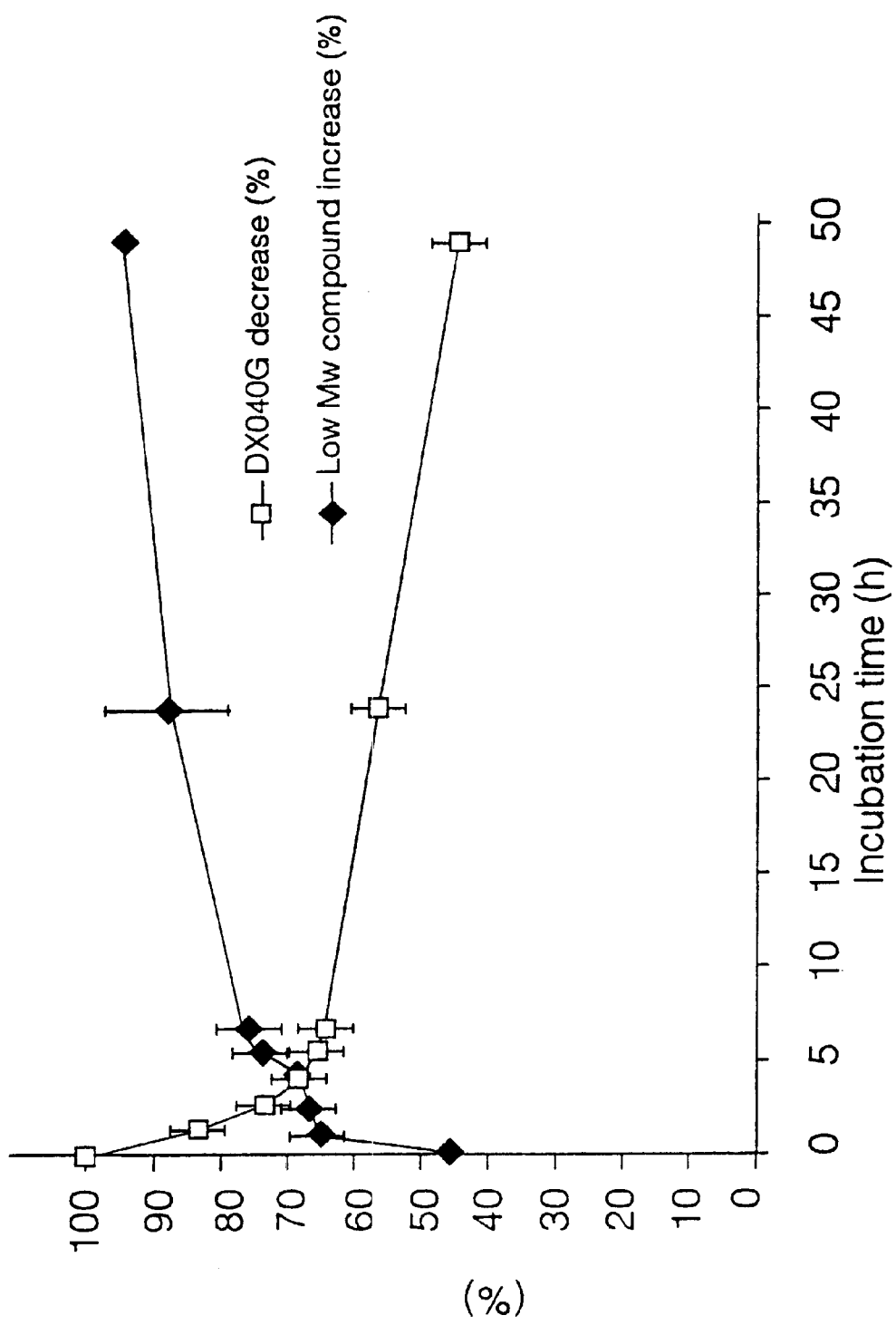
FIG. 11 illustrates DX0 40G degradation and low Mw saccharides release profiles during incubation in rat plasma at 37 C.
Figure 12:
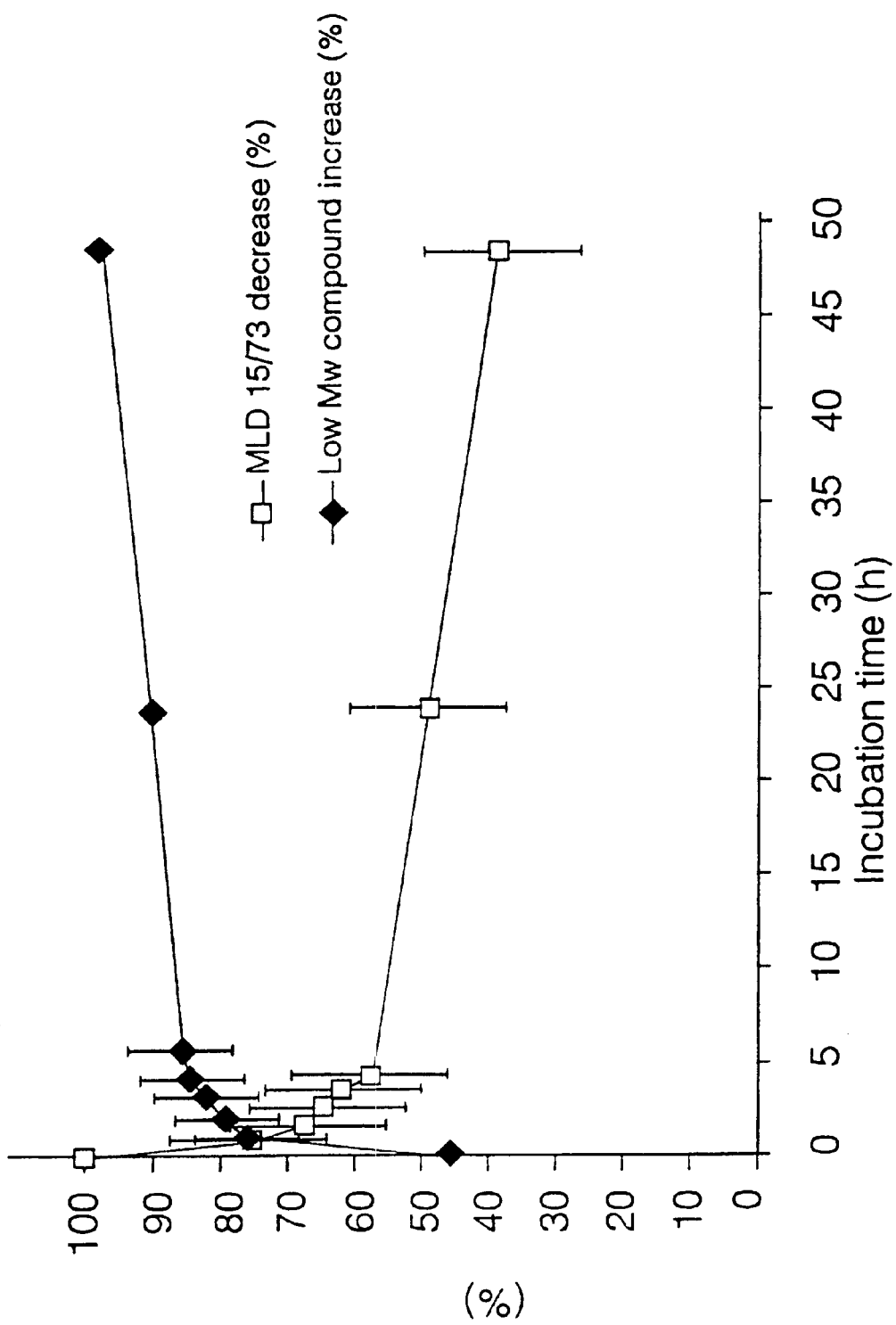
FIG. 12 illustrates MLD 15/73 degradation and low Mw saccharides release profiles in rat plasma at 37 C.

In the absence of enzyme, the dextrin samples at 37° C. did not show any evidence of hydrolysis. FIGS. 9 and 10 illustrate the stability of dextrin of different molecular weights in buffers without enzymes. When plasma enzymes were added samples degraded rapidly over the first hour and more slowly thereafter. Addition of lysosomal enzymes did not cause dextrin degradation. FIGS. 11 and 12 illustrate for samples DX0409 and MLD15/73 respectively, the dextrin degradation and low molecular weight saccharides release during incubation in rat plasma at 37° C.

Example 8.2

Degradation of $^{125}$I-labelled Dextrin Measured by PD10 GPC

Method

Figure 13:
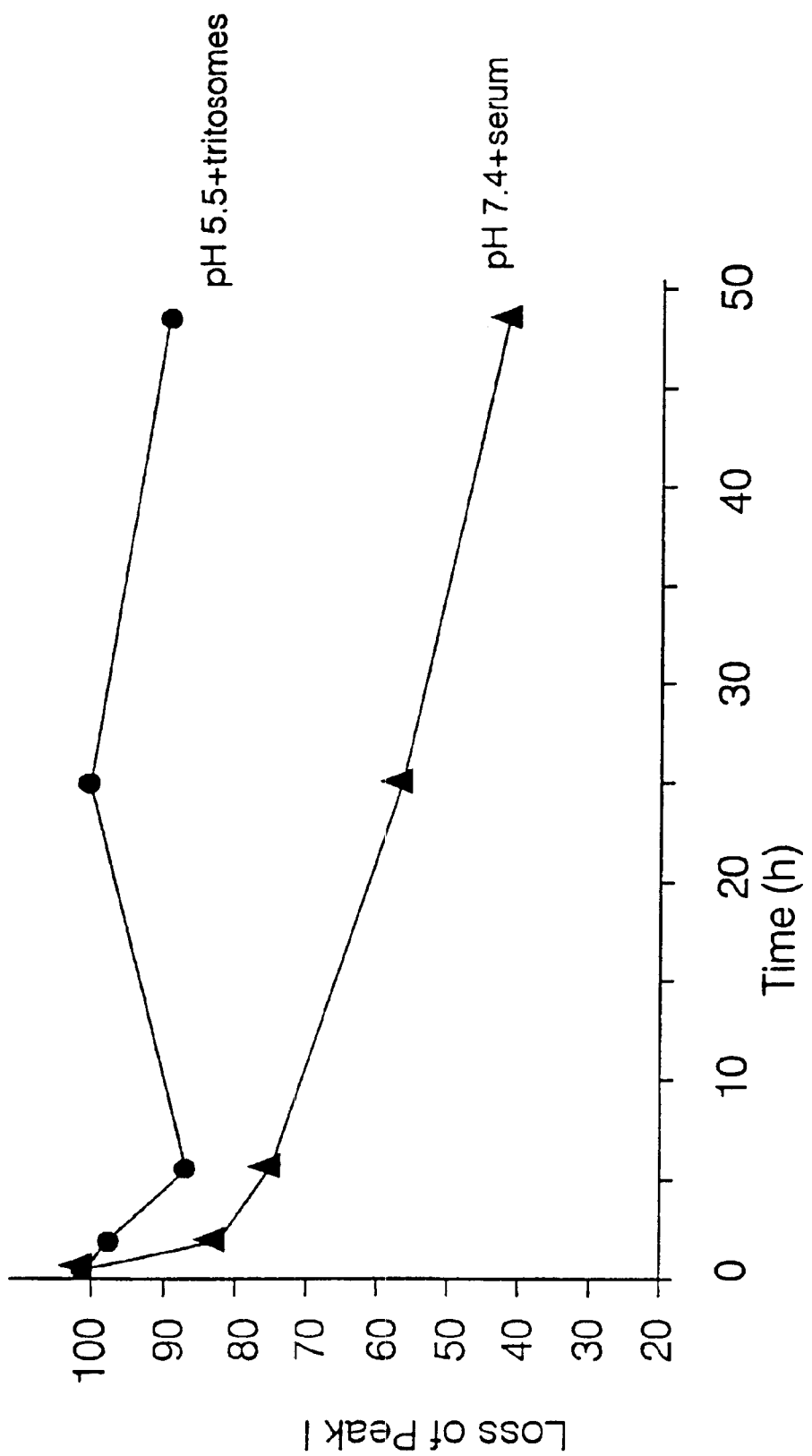
FIG. 13 illustrates degradation of dextrin MD 15/73.

The radiolabelled dextrin sample prepared for the body distribution studies was also incubated with plasma and lysosomal enzymes and samples subjected to PD10 Sephadex chromatography to evaluate the rate of degradation. Fractions eluting from the column were assayed for radioactivity and the results expressed as the percentage decrease in peak one (the polymer peak). The results for dextrin sample MD15/73 are illustrated in FIG. 13.

Results

Although the polymer sample degraded rapidly in the presence of plasma enzymes the product appeared stable in the presence of lysosomal enzymes.

What is claimed is:

1. A polymer-drug conjugate in which the polymer is the polysaccharide dextrin which is covalently linked either directly or indirectly to the drug and the drug is doxorubicin.

2. A polymer-drug conjugate in which the polymer is the polysaccharide dextrin which is covalently linked either directly or indirectly to the drug and the dextrin is a non-cyclic dextrin.

3. The polymer-drug conjugate according to claim 1 or 2 wherein a percentage of alpha-1,6 linkages in the dextrin is less than 10%.

4. The polymer-drug conjugate according to claim 3 wherein the percentage of alpha-1,6 linkages in the dextrin is less than 5%.

5. The polymer-drug conjugate according to claim 1 or 2 wherein a weight average molecular weight of the dextrin is in the range from 1,000 to 200,000.

6. The polymer-drug conjugate according to claim 5 wherein the weight average molecular weight of the dextrin is in the range from 2,000 to 55,000.

7. The polymer-drug conjugate according to claim 1 or 2 wherein the dextrin contains more than 15% of polymers of a degree of polymerization greater than 12.

8. The polymer-drug conjugate according to claim 7 wherein the dextrin contains more than 50% of polymers of DP greater than 12.

9. The polymer-drug conjugate according to claim 1 or 2 wherein a drug loading on the polymer is from 0.5 to 99.5 mole %.

10. The polymer-drug conjugate according claim 1 or 2 wherein a targeting group is attached either directly or indirectly to said polymer.

11. The polymer-drug conjugate according to claim 10 wherein a ratio of drug to targeting group is from 1:99 to 99:1.

12. The polymer-drug conjugate according to claim 1 or 2 wherein the dextrin is water soluble or at least forms a suspension in water.

13. The polymer-drug conjugate according to claim 1 or 2 wherein the dextrin used is in the form of unsubstituted dextrin.

14. The polymer-drug conjugate according to claim 1 or 2 wherein the dextrin is substituted by at lease one negatively charged, neutral, or positively charged substituent group.

15. The polymer-drug conjugate according to claim 14 wherein the substituent group comprises a sulphate group.

16. The polymer-drug conjugate according to claim 15 wherein the polysaccharide dextrin is substituted with at least one sulphate group per saccharide (glucose) unit.

17. A pharmaceutical composition comprising the dextrin-drug conjugate of claim 1 or 2 and a pharmaceutically acceptable excipient or diluent therefor.

18. The pharmaceutical composition according to claim 17 in the form of an aqueous solution or suspension.

19. A method of treating a cancer, comprising administering to a subject a therapeutically effective amount of the polymer-drug conjugate of claim 1 or 2 in the treatment of a cancer in connection with which the drug is effective.

20. A method of treating an animal subject, including a human being, the method comprising treating the animal subject with a pharmaceutically effective dose of the dextrin-drug conjugate of claim 1 or 2.

21. The method according to claim 20 wherein the conjugate is administered intravenously, intraperitoneally, orally, parenterally or by topical application.

22. A method of preparing a polymer-drug conjugate as claimed in claim 1 or 2, the method comprising succinoylating dextrin and reacting the succinoylated dextrin with the drug or reactive derivative thereof.

23. The method according to claim 22 wherein the dextrin is dissolved in anhydrous dimethyl formamide.

24. The method according to claim 23 wherein succinoylating dextrin comprises contacting the dissolved dextrin with dimethyl amino pyridine and succinic anhydride.

25. The method according to claim 24 further comprising after succinoylating the dextrin, purging a succinoylated dextrin mixture with an inert gas.

26. The method according to claim 25 wherein succinoylating dextrin is allowed to take place over a prolonged period.

27. The method according to claim 26 wherein said prolonged period is at least 12 hours.

28. The method according to claim 22 wherein the succinoylated dextrin is reacted with doxorubicin hydrochloride to form the polymer-drug conjugate.

29. A conjugate of a dextrin and a biologically active agent in which the dextrin is covalently linked either directly or indirectly to the biologically active agent and the dextrin is a non-cyclic dextrin.

30. A conjugate according to claim 29 wherein the biologically active agent is an imaging agent, a diagnostic agent, or a targeting agent.

31. A conjugate according to claim 29 wherein the biologically active agent is tyrosinamide.

32. A conjugate according to claim 29 wherein the biologically active agent is biotin.

* * * * *